United States Patent [19]
Schmalstieg et al.

[11] Patent Number: 5,705,593
[45] Date of Patent: Jan. 6, 1998

[54] DIPHENYLMETHANE DIISOCYANATE BASED POLYISOCYANATES CONTAINING ALLOPHANATE GROUPS AND HAVING BLOCKED ISOCYANATE GROUPS

[75] Inventors: Lutz Schmalstieg; Josef Pedain; Theodor Engbert, all of Köln; Holger Casselmann, Bergisch Gladbach; Frank Kobelka, Leverkusen, all of Germany

[73] Assignee: Bayer Aktiengesellschaft, Leverkusen, Germany

[21] Appl. No.: 709,801

[22] Filed: Sep. 10, 1996

[30] Foreign Application Priority Data

Sep. 18, 1995 [DE] Germany ............ 195 34 624.6

[51] Int. Cl.⁶ .......... C08G 18/80; C07C 273/18
[52] U.S. Cl. .......... 528/45; 528/49; 560/25; 560/26; 560/359
[58] Field of Search .......... 528/45, 84, 49; 560/25, 26, 359

[56] References Cited

U.S. PATENT DOCUMENTS

| | | |
|---|---|---|
| 4,007,215 | 2/1977 | Hartmann et al. |
| 4,101,530 | 7/1978 | Burkhardt et al. .......... 528/45 |
| 4,132,843 | 1/1979 | Dalibor .......... 528/45 |
| 4,177,342 | 12/1979 | Bock et al. .......... 528/45 |
| 4,332,965 | 6/1982 | Dalibor .......... 560/169 |
| 4,373,081 | 2/1983 | Nachtkamp et al. .......... 528/45 |
| 4,439,593 | 3/1984 | Kelso et al. .......... 528/45 |
| 4,507,427 | 3/1985 | Pottes et al. .......... 528/45 |
| 5,319,053 | 6/1994 | Slack et al. .......... 528/45 |
| 5,440,003 | 8/1995 | Slack .......... 528/45 |
| 5,574,122 | 11/1996 | Yeske et al. .......... 528/45 |
| 5,576,411 | 11/1996 | Yeske et al. .......... 528/45 |

FOREIGN PATENT DOCUMENTS

| | | |
|---|---|---|
| 649866 | 4/1995 | European Pat. Off. |
| 2639491 | 2/1978 | Germany |
| 1442024 | 7/1976 | United Kingdom |
| 1523103 | 8/1978 | United Kingdom |

*Primary Examiner*—John M. Cooney, Jr.
*Attorney, Agent, or Firm*—Joseph C. Gil; Thomas W. Roy

[57] ABSTRACT

The present invention relates to polyisocyanates prepared from diphenylmethane diisocyanate wherein at least 95% of the isocyanate groups are blocked with diethyl malonate and wherein the polyisocyanates have, based on solids, A) a content of unblocked and blocked isocyanate groups (calculated as NCO) of 9% to 13%, B) a content of allophanate groups (calculated as $C_2HN_2O_3$, molecular weight 101) of 3% to 9% and C) a calculated average functionality of 2.0 to 2.5.

The present invention also relates to a process for the production of these polyisocyanates and to their use as crosslinking agents for organic polyhydroxyl compounds in polyurethane stoving lacquers.

13 Claims, No Drawings

1

DIPHENYLMETHANE DIISOCYANATE BASED POLYISOCYANATES CONTAINING ALLOPHANATE GROUPS AND HAVING BLOCKED ISOCYANATE GROUPS

BACKGROUND OF THE INVENTION

1. Field of the Invention

The present invention relates to novel polyisocyanates prepared from diphenylmethane diisocyanate and in which at least 95% of the isocyanate groups are blocked, to a process for their production and to their use as crosslinking agents in polyurethane stoving lacquers.

2. Description of the Prior Art

It is known to use blocked polyisocyanates for the production of thermally curable polyurethane coatings (for example *Kunststoff-handbuch*, volume VII, *Polyurethane*, Carl Hanser Verlag, Munich 1966, pages 11–13 and 21 et seq.). A range of compounds are described which are suitable for reversibly blocking isocyanates. Of these, the class of CH-acid compounds (for example malonic and acetoacetic acid esters) is of particular significance due to their chemical and physiological properties (for example, see DE-A 2,342,603, 2,436,872, 2,550,156, 2,612,783, 2,612, 784, 2,612,785). DE-A 2,550,156 and DE-A 2,639,491 describe polyurethane stoving lacquers based on aliphatic polyisocyanates blocked with malonic acid esters or acetoacetic acid esters and on organic polyhydroxyl compounds. According to the teaching of DE-A 3,046,409, polyurethane stoving lacquers based on aliphatic polyisocyanates are, however, not suitable for the production of coatings with increased impact and shock resistance. In order to produce such coatings, it is advantageous to use polyisocyanates of the diphenylmethane series according to DE-A 3,046,409.

Even the coating systems of this latter publication are associated with disadvantages: the blocked polyisocyanate crosslinking agents described therein have inadequate non-crystallizing properties, such that they must be blended with a polyol component. Because the blocked polyisocyanates are already blended with a polyol, which predetermines the properties of the resulting coatings, only few options remain open to the processor for adapting the coating composition to the intended application.

Secondly, testing performed by the inventors has revealed that the coating compositions according to DE-A 3,046,409 cure with a slightly textured surface, such that the coatings are not optimally suited for overcoating with high gloss lacquers.

An object of the invention is to provide improved diethyl malonate blocked polyisocyanate crosslinking agents based on diphenylmethane diisocyanate, which are distinguished by good non-crystallizing properties and by excellent levelling on the substrate.

This object may be obtained with the blocked polyisocyanates according to the invention.

SUMMARY OF THE INVENTION

The present invention relates to polyisocyanates prepared from diphenylmethane diisocyanate wherein at least 95% of the isocyanate groups are blocked with diethyl malonate and wherein the polyisocyanates have, based on solids, A) a content of unblocked and blocked isocyanate groups (calculated as NCO) of 9% to 13%, B) a content of allophanate groups (calculated as $C_2HN_2O_3$, molecular weight 101) of 3% to 9% and C) a calculated average functionality of 2.0 to 2.5.

The present invention also relates to a process for the production of these polyisocyanates by reacting diphenylmethane diisocyanate with monoalcohols, optionally blended with minor amounts of diols, to form urethane groups, converting the urethane groups to allophanate groups in the presence of a catalyst and subsequently blocking at least 95% of the isocyanate groups with diethyl malonate.

Finally, the present invention relates to the use of these polyisocyanates as crosslinking agents for organic polyhydroxyl compounds in polyurethane stoving lacquers.

DETAILED DESCRIPTION OF THE INVENTION

The blocked polyisocyanates according to the invention are reaction products of excess molar amounts of diphenylmethane diisocyanate with monoalcohols, optionally mixed with small quantities of diols.

4,4'-diphenylmethane diisocyanate is a suitable starting diisocyanate, optionally mixed with up to 60 wt. % of 2,4'-diphenylmethane diisocyanate and less than 6 wt. % of 2,2'-diphenylmethane diisocyanate. It is preferred to use a purer form of 4,4'-diphenylmethane diisocyanate containing less than 2 wt. % of 2,4'-diphenylmethane diisocyanate and less than 0.5 wt. % of 2,2'-diphenylmethane diisocyanate.

Before blocking, diphenylmethane diisocyanate is partially reacted with monoalcohols, optionally mixed with small quantities of diols, in the presence of a catalyst to produce a polyisocyanate containing allophanate groups.

Monoalcohols having 2 to 22, preferably 2 to 10 carbon atoms, which may optionally contain ether and/or ester groups, are used as the alcohol component. Monohydric alcohols having 4 to 10 carbon atoms which are liquid at room temperature and do not contain ether or ester groups are preferably used.

Suitable monoalcohols include ethanol, n-propanol, i-propanol, n-butanol, i-butanol, n-hexanol, 2-ethylhexanol, n-octanol, n-decanol, n-dodecanol, n-hexadecanol and ethyl lactate.

Also suitable are monohydric alcohols containing ether groups, which may be obtained by ethoxylating and/or propoxylating the previously disclosed monohydric alcohols. Examples include diethylene glycol monobutyl ether. Mixtures of the preceding alcohol may also be used.

The monoalcohols may be mixed with minor amounts of diols during production of the allophanates. Suitable diols include 1,2-ethanediol, 1,2-propanediol, 1,4- or 1,3-butanediol, 1,6-hexanediol, 2-ethyl-1,3-hexanediol, 1,8-octanediol and also dimer fatty alcohols. Diols containing ether groups may also be used, such as diethylene glycol, triethylene glycol, tetraethylene glycol, dipropylene glycol and tripropylene glycol. Mixtures of the preceding diols may also be used.

The quantity of diol which may also be used according to the invention is generally less than 80 mole %, preferably less than 50 mole %, of the quantity of monoalcohol. More preferably, the process is carried out without the addition of diols such that the resulting polyisocyanate containing allophanate groups is difunctional. These difunctional products permit excellent levelling of the resulting coatings on the substrate.

The reaction of the diphenylmethane diisocyanate with the alcohol component is performed in the presence of catalysts which promote allophanate formation. The catalyst may be added prior to urethane formation. Suitable catalysts include metal compounds from main groups 3 and 4 and subgroups 1, 2, 6 and 8 of Mendeleev's periodic system of elements, which are soluble in the reaction mixture (for example, those set forth in U.S. Pat. No. 3,769,318). Tin(II) octoate, zinc stearate and zinc acetylacetonate are preferably used in quantities of 20 to 2000 ppm, preferably of 20 to 200 ppm, based on the weight of the reaction mixture. During the reaction the presence of compounds having an alkylating action, as described in U.S. Pat. No. 3,769,318, is less preferred.

Preferably, the polyisocyanates used to prepare the blocked polyisocyanate mixtures according to the invention exclusively contain allophanate structures and are substantially free of urethane, isocyanurate and/or carbodiimide structures. The presence or absence of these structures may be determined by $^{13}C$ NMR spectroscopy.

Allophanate formation is carried out at temperatures of up to 160° C. The preferred temperature for allophanate formation is 80° to 120° C. Once the calculated NCO content for allophanate formation has been reached, the reaction is terminated, preferably by adding a catalyst poison. Suitable catalyst poisons include compounds having an alkylating or acylating action, such as p-toluene-sulphonic acid methyl ester, dimethyl sulphate, benzoyl chloride and isophthalic acid dichloride. The catalysts poisons are preferably used in at least equimolar quantities, based on the amount of catalyst.

The resulting polyisocyanate mixtures containing allophanate groups are obtained in the form of yellowish, low viscosity liquids having an NCO content of 14.5% to 28.5%. In the second stage of the process according to the invention, they are directly reacted in a blocking reaction with diethyl malonate. The blocking reaction is performed in known manner (e.g., as described in DE-A 2,342,603, DE-A 2,550, 156) in the presence of basic catalysts, such as sodium phenolate, sodium methylate or other alkali metal alkoxides. Other alkali metal compounds, such as sodium malonate, may also be used as catalysts. The catalysts are added in a quantity of 0.1% to 2%, based on the total weight of the reaction components. The quantity of diethyl malonate should be at least 1 mole per equivalent of isocyanate; however, it is preferred to use a 5 to 20% excess of blocking agent.

The blocking reaction may be performed without solvents or in the presence of solvents which are inert towards isocyanates. Suitable solvents include ethyl acetate, ethylene glycol monomethyl ether acetate, ethylene glycol monoethyl ether acetate, butyl acetate, methoxypropyl acetate, methyl ethyl ketone, toluene, xylene, and the higher boiling hydrocarbon mixtures known from coatings technology. The solvents may be used individually or as a mixture. It is also possible to use plasticizers instead of solvents, e.g., known plasticizers such as phosphoric acid esters, phthalic acid esters and sulphonic acid esters.

The quantity of solvents or plasticizers is preferably selected such that the predominantly or completely blocked polyisocyanates according to the invention have a solids content of 70 to 90 wt. %.

The blocked polyisocyanates according to the invention are highly viscous or resinous products, which are preferably based on 4,4'-diphenylmethane diisocyanate and which are distinguished by excellent non-crystallizing properties.

The blocked polyisocyanates are valuable crosslinking resins for polyhydroxyl compounds in the production of stoving lacquers. Suitable polyhydroxyl compounds for this purpose and details relating to the production and use of such stoving lacquers may be found in the relevant literature, for example, Z. W. Wicks, *Progr. Org. Coat.* 9, page 20 (Applications) 1981.

Coatings prepared from stoving lacquers based on the blocked polyisocyanate crosslinking agents are distinguished by excellent adhesion, elevated elasticity, good surface hardness and especially their levelling properties, which are better than those obtained according to DE-A 3,046,409. Also, the coatings have completely untextured surfaces. By virtue of the stated properties, the blocked polyisocyanates according to the invention are particularly suitable for the production of automotive stoving surfacers.

In the following examples parts and percentages are by weight unless otherwise indicated.

EXAMPLES

Example 1—Production of a blocked polyisocyanate according to the invention 937.5 g of technical grade 4,4'-diphenylmethane diisocyanate were melted. 74 g of n-butanol were added dropwise to the clear melt at 80° C. Once the exothermic reaction had died down, 0.05 g of zinc acetylacetonate were added and the mixture was stirred at 80° C. for approximately 5 hours until allophanate formation was complete. The reaction mixture had an NCO content of 22.5%. After 0.05 g of isophthalic acid dichloride were added, 885 g of diethyl malonate were added, which reduced the temperature of the reaction mixture to 50° C. At this temperature, a solution of 3 g of a catalyst solution in 87.5 g of diethyl malonate was slowly added dropwise. The catalyst solution was a 30% solution of sodium methylate in methanol. Once the exothermic reaction has died down, the mixture was stirred for a further 7 hours at 50° C. and then diluted with a mixture of equal parts of butyl acetate and Solvesso 100 solvent (an aromatic hydrocarbon mixture from Exxon Corp.). The resulting blocked polyisocyanate crosslinking agent did not crystallize at 0° C. and had the following properties:

Solids content: 80%

Viscosity: 750 mPa.s (23° C.)

Free NCO content: 0.1% (based on solution)

Blocked NCO content: 9.2% (calculated, based on solution)

Functionality: 2 (calculated)

Allophanate group content: 5.1% (calculated, based on resin solids)

Example 2—Production of a blocked polyisocyanate according to the invention

Example 1 was repeated with the exception that 118 g. of ethyl lactate were used instead of n-butanol.

The resultant polyisocyanate crosslinking agent did not crystallize at 0° C. and, after dilution, had the following properties:

Solids content: 80%

Viscosity: 1600 mPa.s (23° C.)

Free NCO content: approx. 0.1% (based on solution)

Blocked NCO content: 9.1% (calculated, based on solution)

Functionality: 2 (calculated)

Allophanate group content: 5.0% (calculated, based on resin solids)

Example 3—Production of a blocked polyisocyanate according to the invention

Example 1 was repeated using the following materials:

| 1250 g of a mixture of | 82% 4,4'-diphenylmethane diisocyanate |
| --- | --- |
| | 17.5% 2,4'-diphenylmethane diisocyanate |
| | 0.5% 2,2'-diphenylmethane diisocyanate |
| 130 g of 2-ethylhexanol | |
| 1440 g of diethyl malonate | |
| (total quantity). | |

The resulting polyisocyanate crosslinking agent did not crystallize at a temperature of 10° C. and, after dilution, had the following properties:

Solids content: 80%

Viscosity: 2500 mPa.s (23° C.)

Free NCO content: not detectable

Blocked NCO content: 9.5% (calculated, based on solution)

Functionality: 2 (calculated)

Allophanate group content: 3.6% (calculated, based on resin solids)

Example 4—Production of a stoving lacquer according to the invention 135.3 parts of polyester solution present as a 65% solution in a 31.5:3.5 solvent mixture of Solvesso 100 solvent and i-butanol and having a hydroxyl content of 1.7% (calculated as OH), an acid number of 5 and a viscosity of 2600 mPa.s at 23° C. (Alkynol 1665, available from Bayer AG) were combined with 180 parts of barium sulphate (Blanc fixe micro available from Sachtleben-Chemie, Duisburg), 60 parts of RAL 7000 coloring pigment mixture containing 54.78 parts of titanium dioxide (R-KB-4 available from Bayer AG), 3.84 parts of iron oxide pigment (Bayferrox 130 F available from Bayer AG), 0.9 parts of a coloring pigment (Heliogenblau L7101 F available from BASF AG, Ludwigshafen), 0.48 parts of an iron oxide pigment (Bayferrox 3910 F available from Bayer AG), 1.5 parts of a dispersion auxiliary (Antiterra U, 50% solution, available from Byk-Chemie, Wesel), 0.3 parts of silica gel (Aerosil R 972 available from Degussa, Frankfurt/Main), 40.3 parts of 1-methoxy-2-propyl acetate, 40.3 parts of butyl acetate and 40.3 parts of xylene and dispersed for 45 minutes in a bead mill with cooling such that the temperature of the material being ground did not exceed 50° C.

The resulting paste was combined with a further 108.3 parts of a polyester solution present as an 80% solution in butyl acetate and having a hydroxyl content of 3.4% (calculated as OH), an acid number of 1 and a viscosity of 3000 mPa.s (23° C.) (Desmophen 670, available from Bayer AG), 3 parts of a levelling agent (Byk 358, 50% solution, available from Byk-Chemie, Wesel), 160.5 parts of the polyisocyanate crosslinking agent from example 1 and diluted with stirring with 14 parts of 1-methoxy-2-propyl acetate, 14 parts of butyl acetate and 14 parts of xylene.

The resultant coating composition spray applied well and exhibited excellent levelling properties.

When applied to metal sheets coated with an electrocoating lacquer, the film had no surface texture. Blister-free, dry film thicknesses of >45 μm without surface defects were produced in a single operation. The coating cured at stoving temperatures of as low as 130° C. The optimum stoving temperature for this coating composition was 140° C.

Physical properties of the coating after 30 minutes' stoying at 130° C.:

König pendulum hardness (DIN 53117): 152 sec

Erichsen indentation (DIN 53156): 10.0 mm

Impact test (ASTM D2794): >80 i/p

The coating exhibited good adhesion to the substrate (electrocoated lacquer) and good intercoat adhesion to lacquer base coats and topcoats.

The film was found to have elevated resistance to stone impact in the grading system set out in the VDA multi-impact test (Verband der Automobilindustrie, model 508, 2 times 500 g steel pellets, 1.5 bar).

Example 5—Comparison example according to DOS 3,046,409.

Example 1 was repeated, with the exception that the allophanate formation step was omitted, from the following materials:

1250 g of 4,4'-diphenylmethane diisocyanate 1760 g of diethyl malonate (total quantity)

After dilution the resulting blocked polyisocyanate crosslinking agent had the following properties:

Viscosity: 1400 mPa.s (23° C.)

Free NCO content: 0.15% (relative to solution)

Blocked NCO content: 11.1% (calculated, relative to solution)

The product crystallized after storage for 7 days at room temperature.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A The polyisocyanate prepared from diphenylmethane diisocyanate wherein at least 95% of the isocyanate groups are blocked with diethyl malonate and wherein the polyisocyanate has, based on solids, A) a content of unblocked and blocked isocyanate groups (calculated as NCO) of 9% to 13%, B) a content of allophanate groups (calculated as $C_2HN_2O_3$, molecular weight 101 ) of 3% to 9% and C) a calculated average functionality of 2.0 to 2.5.

2. The polyisocyanate of claim 1 wherein the polyisocyanate is prepared from 4,4'-diphenylmethane diisocyanate.

3. The polyisocyanate of claim 1 wherein the polyisocyanate has an average calculated functionality of 2.

4. The polyisocyanate of claim 2 wherein the polyisocyanate has an average calculated functionality of 2.

5. A process for the production of a polyisocyanate having, based on solids,

A) a content of unblocked and blocked isocyanate groups (calculated as NCO) of 9% to 13%, B) a content of allophanate groups (calculated as $C_2HN_2O_3$, molecular weight 101 ) of 3% to 9% and C) a calculated average functionality of 2.0 to 2.5, which comprises reacting diphenylmethane diisocyanate with a monoalcohol, optionally blended with a minor amount of a diol, to form urethane groups, converting the urethane groups to allophanate groups in the presence of a catalyst and subsequently blocking at least 95% of the isocyanate groups with diethyl malonate.

6. The process of claim 5 wherein said monoalcohol has 2 to 22 carbon atoms and the reaction is carried out while maintaining an NCO/OH equivalent ratio of 5:1 to 12:1 at temperatures of up to 160° C.

7. A polyurethane stoving lacquer containing as binder an organic polyhydroxyl compound and, as crosslinking agent, the polyisocyanate of claim 1.

8. A polyisocyanate i) which is prepared from diphenylmethane diisocyanate and a monoalcohol which contains 2 to 22 carbons and which may only be substituted with ether or ester groups, ii) wherein at least 95% of the isocyanate groups are blocked with diethyl malonate and iii) wherein the polyisocyanate has, based on solids, A) a content of unblocked and blocked isocyanate groups (calculated as NCO) of 9% to 13%, B) a content of allophanate groups (calculated as $C_2HN_2O_3$, molecular weight 101 ) of 3% to 9% and C) a calculated average functionality of 2.0 to 2.5.

9. The polyisocyanate of claim 8 wherein the polyisocyanate is prepared from 4,4'-diphenylmethane diisocyanate.

10. The polyisocyanate of claim 8 wherein the polyisocyanate has an average calculated functionality of 2.

11. The polyisocyanate of claim 9 wherein the polyisocyanate has an average calculated functionality of 2.

12. A process for the production of a polyisocyanate having, based on solids,

A) a content of unblocked and blocked isocyanate groups (calculated as NCO) of 9% to 13%, B) a content of allophanate groups (calculated as $C_2HN_2O_3$, molecular weight 101) of 3% to 9% and C) a calculated average functionality of 2.0 to 2.5, which comprises reacting diphenylmethane diisocyanate with a monoalcohol which contains 2 to 22 carbon atoms and which may only be substituted with ether or ester groups, optionally blended with a minor amount of a diol, to form urethane groups, converting the urethane groups to allophanate groups in the presence of a catalyst and subsequently blocking at least 95% of the isocyanate groups with diethyl malonate.

13. The process of claim 12 wherein the reaction is carried out while maintaining an NCO/OH equivalent ratio of 5:1 to 12:1 at temperatures of up to 160° C.

* * * * *